(12) United States Patent
Unger et al.

(10) Patent No.: US 9,840,447 B2
(45) Date of Patent: Dec. 12, 2017

(54) METHOD FOR EXTRACTING HYDROCARBONS WITH MEDIUM CHAIN LENGTHS, AND THE USE OF THE SAME

(71) Applicant: Fraunhofer-Gesellschaft zur Förderung der angewandten Forschung e.V., München (DE)

(72) Inventors: Christoph Unger, Wesel (DE); Andreas Menne, Mülheim a.d. Ruhr (DE); Axel Kraft, Oer-Erkenschwick (DE); Volker Heil, Oberhausen (DE)

(73) Assignee: Fraunhofer-Gesellschaft zur Förderung der angewandten Forschung e.V., Munich (DE)

( * ) Notice: Subject to any disclaimer, the term of this patent is extended or adjusted under 35 U.S.C. 154(b) by 458 days.

(21) Appl. No.: 14/349,921

(22) PCT Filed: Oct. 10, 2012

(86) PCT No.: PCT/EP2012/070055
§ 371 (c)(1),
(2) Date: Apr. 4, 2014

(87) PCT Pub. No.: WO2013/053754
PCT Pub. Date: Apr. 18, 2013

(65) Prior Publication Data
US 2014/0249337 A1 Sep. 4, 2014

(30) Foreign Application Priority Data
Oct. 10, 2011 (DE) .................. 10 2011 115 377

(51) Int. Cl.
*C07C 27/00* (2006.01)
*C07C 1/207* (2006.01)
*C10G 3/00* (2006.01)

(52) U.S. Cl.
CPC ............ *C07C 1/2078* (2013.01); *C10G 3/44* (2013.01); *C07C 2521/18* (2013.01); *C10G 2300/202* (2013.01); *C10G 2400/08* (2013.01); *Y02P 30/20* (2015.11)

(58) Field of Classification Search
CPC .......... C07C 1/00; C07C 1/02; C07C 1/2072; C07C 1/2074; C07C 1/2076; C07C 1/2078; C07C 1/22; C07C 1/24; C07C 2521/18; C10L 1/02; C10L 1/18; C10L 1/1802; C10L 1/19; C10L 1/182; C10L 1/188
USPC ................. 588/638, 639, 16, 701, 240, 501; 44/445 R, 401, 402, 388, 308
See application file for complete search history.

(56) References Cited

U.S. PATENT DOCUMENTS

| 1,960,951 A | 5/1934 | Oppenheim |
| 1,991,955 A | 2/1935 | Ralston |
| 2008/0034645 A1 | 2/2008 | Bressler |
| 2010/0296997 A1 | 11/2010 | Parker et al. |
| 2011/0237854 A1 | 9/2011 | Heil et al. |

FOREIGN PATENT DOCUMENTS

| DE | 103 27 059 | 1/2005 |
| DE | 10 2008 049778 | 4/2010 |
| EP | 1 724 325 | 11/2006 |

OTHER PUBLICATIONS

EP 12 774 998.4, published as EP2766456 on Aug. 20, 2014, Examination Report, dated May 8, 2015.
Sudaryanto et al., "High surface area activated carbon prepared from cassava peel by chemical activation", Bioresource Technology, Elsevier BV, GB, vol. 97, No. 5, 2006, pp. 734-739, XP027965419.
CN App. No. 201280049768.7, filed Oct. 10, 2012, translation of First Office Action, dated Feb. 2, 2015.
CN App. No. 201280049768.7, filed Oct. 10, 2012, translation of search report, 3 pages.
Li Jinchao et al., The Evolution and Hydrocarbon-forming Mechanism of Organic Matter of Continental Facies, Petroleum Industry Press, published Apr. 30, 1984, pp. 89-98.
Zhou Jianwei et al., New Energy Chemistry, Zhengzhou University Press, published Aug. 31, 2009, pp. 95-98.
EP 12 774 998.4, published as EP2766456 on Aug. 20, 2014, Office Action, dated Dec. 8, 2015, 4 pages.
CN App. No. 201280049768.7, filed Oct. 10, 2012, translation of Second Office Action, dated Nov. 20, 2015.
CN App. No. 201280049768.7, filed Oct. 10, 2012, translation of supplementary search report, 2 pages.
International Search Report, PCT/EP2012/070055, filed Oct. 10, 2012.
Festel et al., "Decarboxylation of fatty oils and fatty acids—a novel route towards bio-jet fuel", Poster presented at the RRB-8, Toulouse, France, Jan. 4, 2012.
Fu et al., "Activated carbons for hydrothermal decarboxylation of fatty acids", ACS Catalysis, Bd. 1, Nr. 3, Jan. 1, 2011.

*Primary Examiner* — Sharon Pregler
(74) *Attorney, Agent, or Firm* — Brinks Gilson & Lione

(57) ABSTRACT

The invention relates to a method for extracting hydrocarbon mixtures that have an increased proportion of hydrocarbons of a medium chain length (8 to 16 carbon atoms), or the corresponding pure compounds. Firstly, a starting material is provided that includes at least 50 wt. % unsaturated hydrocarbon compounds having oxygen. The compounds include olefin fragments of the formula —$C_1C_xH_{2x}$—CH=CH—$C_yH_{2y+1}$ with at least 14 carbon atoms, carbon atom ($C_1$) being saturated with substituted or unsubstituted heteroatoms and/or hydrogen. In a conversion reactor, this starting material is brought into contact with a porous catalyst based on carbon, in the absence of oxygen, and at a temperature of between 200 and 800° C.; and a product mixture that contains hydrocarbons is produced containing an increased proportion of hydrocarbons with medium chain lengths. Finally, the product mixture including hydrocarbons is collected and fed to a separating device in which a product separation is carried out.

17 Claims, 10 Drawing Sheets

FIG 1D
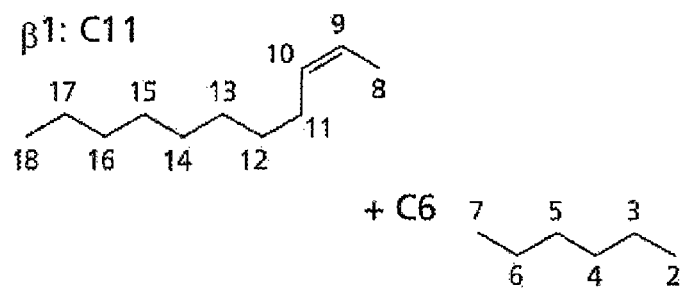
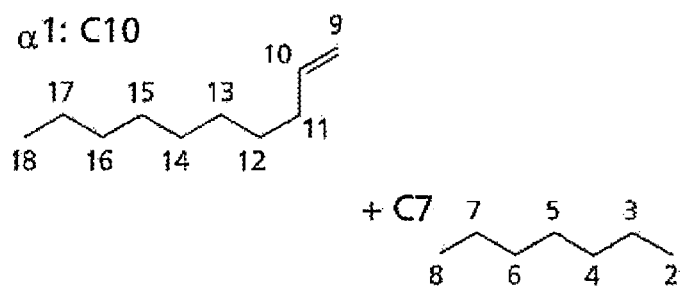
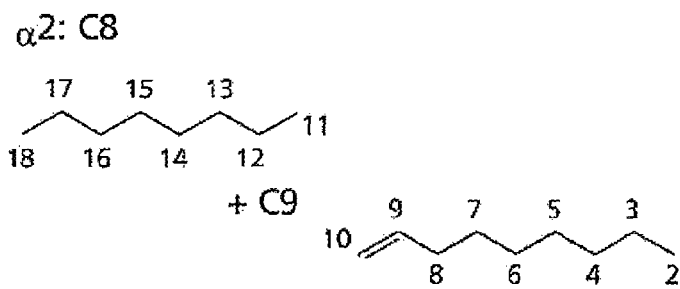
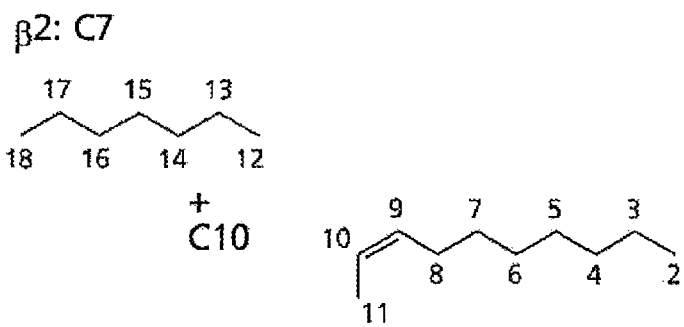

FIG 1L
β1: C9
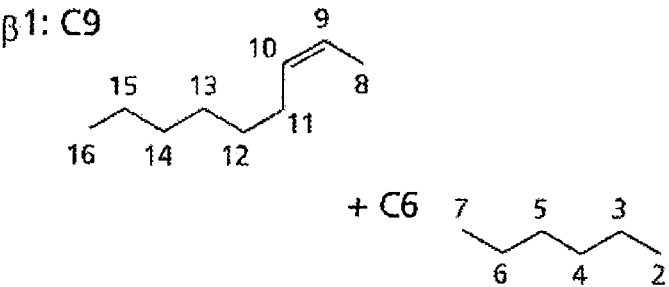
+ C6
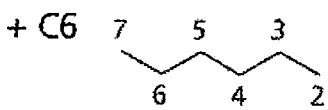
α1: C8
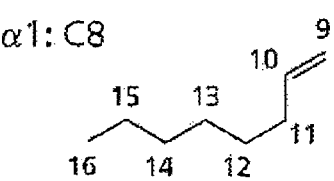
+ C7
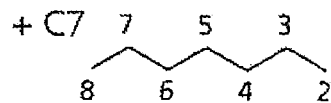
α2: C6
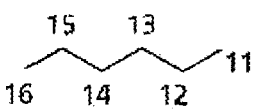
+ C9
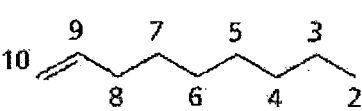
β2: C5
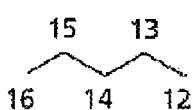
+ C10
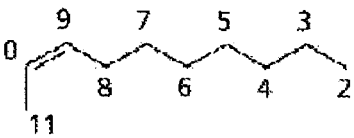

METHOD FOR EXTRACTING HYDROCARBONS WITH MEDIUM CHAIN LENGTHS, AND THE USE OF THE SAME

This application is a National Stage application of International Application No. PCT/EP2012/070055, filed Oct. 10, 2012, the entire contents of which is hereby incorporated herein by reference. This application also claims the benefit under 35 U.S.C. §119 of German Patent Application No. 10 2011 115 377.6, filed Oct. 10, 2011, the entire contents of which is hereby incorporated herein by reference.

The application relates to a method for producing hydrocarbons with medium chain lengths, e.g. hydrocarbons having 8 to 16 carbon atoms. In this method, unsaturated oxygen-containing hydrocarbon compounds are used as the starting material and brought into contact with a porous catalyst based on carbon at elevated temperature. The application further relates to the use of the hydrocarbon mixture obtained using this method, or of pure hydrocarbons obtained therewith, for producing aviation fuel.

BACKGROUND

Hydrocarbons with medium chain lengths are on the one hand essential raw materials for the chemical industry, on the other hand there is also a need for particularly oxygen-free hydrocarbons with medium chain lengths as an important building block for kerosene for use in aviation, for example as "drop-in aviation fuel" and here in particular in the form of biokerosene. Biokerosene is produced according to the prior art for example by hydrogenation of bio-based oils. According to the prior art, it is also known that by reacting fats, oils or fatty acids over porous catalysts, it is possible to obtain either liquid hydrocarbons or else to generate gaseous hydrocarbons in a targeted manner.

For example, DE 103 27 059 A1 and EP 1 724 325 A1 disclose methods in which fat-containing starting materials are brought into contact with an activated carbon fixed bed at elevated temperatures in a reactor. Here, a decarboxylation of the fatty acids present takes place, giving rise to liquid hydrocarbons. In order to arrive at gaseous hydrocarbons, the process parameters and optionally also the processing of the starting material can be modified such that a degradation of the starting materials to gaseous, short-chain hydrocarbons takes place. Increased formation of hydrocarbons with medium chain lengths, however, is not described in the cited documents.

Using the Fischer-Tropsch process, it is possible to produce hydrocarbons with any desired chain length from fat-containing starting materials; however, in this process, the starting material is firstly degraded to $C_1$ segments, from which subsequently hydrocarbons with different chain lengths have to be built up again. This process is accordingly associated with considerable energy expenditure and, moreover, is only economically feasible on a very large scale.

It is therefore an object of the present invention to overcome the disadvantages of the prior art and to provide a method for converting oxygen-containing hydrocarbon compounds or mixtures of oxygen-containing hydrocarbon compounds into hydrocarbons with medium chain lengths. It is a further object of the present invention to provide a method for producing hydrocarbon mixtures that is suitable for producing biokerosene.

At least one of these objects is achieved by the subject matter of the independent claims. Further embodiments and developments are the subject matter of independent claims and are also evident from the description below.

A method for producing pure hydrocarbons with medium chain lengths or hydrocarbon mixtures with an increased fraction of hydrocarbons with medium chain lengths comprises the following steps:

A) Firstly a starting material is provided which comprises at least 50% by weight of unsaturated oxygen-containing hydrocarbon compounds. These unsaturated hydrocarbon compounds have at least in part structural units which satisfy the following specification (these structural units are referred to hereinbelow as olefin fragments since they are responsible, at least in part, for the unsaturated character of the hydrocarbon compounds). The olefin fragments have the formula $-C_1-C_xH_{2x}-CH=CH-C_yH_{2y+1}$ (formula I). The carbon atom $C_1$ in this olefin fragment marks the transition to a heteroatom. Accordingly, the carbon atom $C_1$ is saturated with at least one substituted or unsubstituted heteroatom and optionally also hydrogen. Often, an oxygen atom will be bonded to the carbon atom $C_1$ and this again is then bonded to a carbon atom (such as for example in a fatty acid ester, for example a glyceride) or, together with the carbon atom $C_1$, is a part of a carboxylate group (such as e.g. in a fatty acid). The indices x and y in the given formulae are integers, where x is greater than 1 and y is greater than 0. In other words, it is neither an olefin fragment with a terminal double bond, nor an olefin fragment in which the double bond follows directly on the $C_1$ atom. The olefin fragments are also characterized in that they have at least 14 carbon atoms, in particular 16 to 22 carbon atoms.

Particularly for starting materials which comprise the mixtures of different unsaturated oxygen-containing hydrocarbon compounds, but optionally also in the case of starting materials which contain just one oxygen-containing hydrocarbon compound which is a di- or triglyceride, several different olefin fragments are present. Hereinbelow, in this connection the olefin fragment with the largest molar fraction with $k_1$ mol % is referred to as main component $K_1$. Further olefin fragments are referred to as $K_2$ to $K_x$ and have a fraction of $k_2$ to $k_x$ mol %. For determining the increased fraction of hydrocarbons of medium chain length, achieved according to the invention, only those olefin fragments are included here which are present at least in a fraction of 5 mol %. This proviso ensures that a simple determination of an increased fraction is possible, especially since olefin fragments with a low fraction exert only a slight effect on the product spectrum.

In step B) of the method according to the invention, the starting material is contacted with a porous carbon-based catalyst in the absence of oxygen at an elevated temperature in a conversion reactor. An elevated temperature is to be regarded here as being in particular a temperature of 200-800° C., preferably 300-600° C. and in particular 350-550° C. Under such conditions, the selected starting material gives a product mixture in which the fraction of hydrocarbons with medium chain lengths, i.e. in particular the fraction of at least one (optionally pure) hydrocarbon having 8 to 16 carbon atoms, has an increased fraction.

Finally, in a part step C), the hydrocarbon-containing product mixture is collected and fed to a separating device in which product separation takes place.

According to the invention, an increased fraction of hydrocarbons with medium chain lengths is understood as meaning that at least the fraction of one of the components with 8, 9, 10, 11, 12, 13, 14, 15 or 16 or more carbon atoms is increased in the product spectrum. In most cases, the fraction of at least two of these components is increased, often also that of three or more than three of these components. In particular, the component with y+3 carbon atoms occurs to an increased extent in the product spectrum (where y refers to the aforementioned formula of the olefin fragment). For the main component $K_1$ and the other components $K_2$-$K_x$, in each case the corresponding component is ascertained for this with y+3 carbon atoms, which accordingly serves in a way as a "marker". According to the invention, an increased fraction can be detected on two different types, with the first alternative explained below being given preference on account of the simpler accessibility of the required data.

According to the first alternative, an increased fraction of hydrocarbons with medium chain lengths is determined as follows: firstly, for the main component $K_1$ and each further component $K_2$ to $K_x$ optionally to be used (with more than 5 mol % fraction), the aliphatic product compounds $\beta$, which all have y+3 carbon atoms, are ascertained (for the main component thus the product compounds $\beta_1$, for the further component $K_2$ the product compounds $\beta_2$ etc.). These are the marker compounds which have a particularly high fraction, where, as aliphatic product compounds $\beta$, besides the unbranched saturated compounds, only the monounsaturated product compounds of the product mixture are determined, and even only then if their weight fraction in the product mixture is more than 10%, based on the saturated unbranched product compound (lower contents complicate the determination method for the increased fraction unnecessarily and also do not significantly contribute to the result of this determination process, and are thus expediently omitted). The aliphatic product compounds $\beta_x$ with y+3 carbon atoms thus correspond to a hydrocarbon which arises formally by breaking the bond in the $\beta$ position relative to the double bond on the side facing away from the chain end (in which case the product compounds are also included in which formally also a hydrogenation or isomerization of the double bond must take place). According to the invention, it has been established that compounds with such a chain length are formed to a particularly increased degree if the starting material specified above is used. The formal formation by breaking the bond in the $\beta$ position, however, should not be understood herein as being restrictive, but is merely used for the definition of the product compounds $\beta_x$.

Furthermore, for the main component $K_1$ and each further component $K_2$-$K_x$ optionally to be used, also the corresponding product compounds $\delta$, which all have y−1 carbon atoms, are ascertained (for the main component thus the product compounds $\delta_1$, for optionally present further components the product compounds $\delta_2$ etc.). Here as well, as above for the product compounds $\beta$, the unbranched saturated aliphatic product compounds are determined, as are the unbranched monounsaturated aliphatic product compounds if their molar fraction is more than 10%, based on the saturated aliphatic product compounds. The product compounds $\delta$ stand for a product component which is formed to a lesser extent or to a not increased extent and thus constitute an "antimarker". They correspond to the segment which is formed if a bond separation formally takes place in the $\alpha$ position relative to the double bond on the side of the chain end of the product fragment. According to the invention, it was observed that these product compounds $\delta$ are formed in the starting material described above to a particularly low extent (based on the product compounds $\beta$).

According to the first alternative for determining the increased fraction, in a part step b), for all of the product compounds $\beta_x$ and $\delta_x$ thus determined, their molar fractions $n_{\beta x}$ and $n_{\delta x}$ present in the product mixture are then determined. For a starting material in which one main component and two further components are present, for the product compounds $\beta_1$, $\beta_2$ and $\beta_3$, their fractions $n_{\beta 1}$, $n_{\beta 2}$ and $n_{\beta 3}$ in the product mixture are thus determined and for $\delta_1$, $\delta_2$ and $\delta_3$, their fractions $n_{\delta 1}$, $n_{\delta 2}$ and $n_{\delta 3}$ are determined.

According to the first alternative, in a part step c), finally all of the product compounds $\beta_x$ are used to calculate the averaged fraction $\overline{n_\beta}$ and for the product compounds $\delta_x$ the average fraction $\overline{n_\delta}$, with the averaged fraction according to the formula being used for calculating the number average molar mass of a polymer, namely $$\overline{n} = \sum_{i=1}^{x} k_i * n_i.$$

If one main component and two further components are present, then for the three marker product compounds $\beta$ the averaged fraction $\overline{n_\beta}$ is dependent on the molar fraction determined in each case of the main component and of the further components in the starting material and likewise for the antimarker, i.e. the product compounds $\delta$, the averaged fraction $\overline{n_\delta}$ from the three antimarker product compounds.

An increased fraction of hydrocarbons with medium chain lengths (i.e. hydrocarbons having 8 to 16 carbon atoms) is present according to the invention if it applies that $\overline{n_\beta} > 1.15 * \overline{n_\delta}$, i.e. that the average fraction of the marker is at least 15% higher than the average fraction of the antimarker. Preferably, it applies that $\overline{n_\beta} > 1.25 * \overline{n_\delta}$ and particularly preferably that $\overline{n_\beta} > 1.5 * \overline{n_\delta}$; the average fraction of the marker is thus at least 25% or 50% higher than that of the antimarker.

According to a second alternative, an increased fraction of hydrocarbons with medium chain length can also be detected as follows: as above in the first alternative, for a given starting material, the averaged fractions $\overline{n_\beta}$ are determined for the product compounds $\beta_x$ of the main component and all optionally present secondary components. Then, the starting material is hydrogenated by means of hydrogen/palladium catalyst in such a way that the fraction of the double bonds in the starting material is reduced by at least 95% (determination by reference to the iodine number). This material is reacted analogously to the method according to the invention under the same reaction conditions as the nonhydrogenated starting material to give a product mixture in which then, again for the same product compounds $\beta$ as were determined for the nonhydrogenated starting material, the averaged fraction $\overline{n_\beta}^{\#}$ is determined. It then applies that $\overline{n_\beta} > 1.15 * \overline{n_\beta}^{\#}$ (in the case of nonhydrogenated starting material at least 15% more of the marker is formed). Preferably, it applies that $\overline{n_\beta} > 1.25 * \overline{n_\beta}^{\#}$ and particularly preferably that $\overline{n_\beta} > 1.5 * \overline{n_\beta}^{\#}$ (i.e. at least 25% or 50% more of the marker is formed).

The method according to the invention offers for the first time the possibility of obtaining high yields of hydrocarbons with medium chain lengths, that is to say hydrocarbons of 8 to 16 carbon atoms, upon cleavage of compounds such as fats and oils over a porous carbon-containing catalyst by means of targeted selection of the starting material. The methods according to the prior art are essentially designed to cleave fats and similar substances to give long-chain hydrocarbons and/or lead to products in which merely an elimination of the carboxylate group of fatty acids is observed to an increased extent. The methods according to the prior art thus focus in particular on obtaining pure hydrocarbon compounds from a starting material by cleaving off the heteroatoms from the starting materials. A cleavage of carbon-carbon bonds often takes place only to a restricted extent or is even undesired if one disregards the fact that the reaction conditions may also be so drastic that only segments having 1 to 4 carbon atoms are formed to an increased extent. By contrast, it is not described how following elimination for example of the carboxylate group of a fatty acid to an increased extent (only) one further bond break takes place and accordingly an increased formation of hydrocarbons with medium chain lengths.

In the method according to the invention, it has also been recognized that as a result of the targeted use of double bond-containing starting materials, a product spectrum is obtained in which the hydrocarbons which arise as the result of the breakage of bonds that are adjacent to double bonds can be detected to an increased extent. In other words, it has been recognized according to the invention that by using double bond-containing starting materials, shorter products are obtained than when using the corresponding compounds which have a single bond instead of a double bond, i.e. are saturated.

Finally, it has been found according to the invention that particularly monounsaturated olefin fragments are especially suitable for achieving the desired product spectrum. With polyunsaturated compounds, it is often observed that under the conditions prevailing in part step B) a polymerization or other chemical reactions of the double bonds take place, meaning that during cracking of the polyunsaturated olefin fragments, no increased formation of hydrocarbons with medium chain lengths is usually observed.

BRIEF DESCRIPTION OF THE DRAWINGS

FIG. 1D shows products of the present invention produced during cleavage of the $\alpha 1$, $\alpha 2$, $\beta 1$ and $\beta 2$ bond in the molecule of FIG. 1A according to an embodiment of the present invention.

FIG. 1L shows products produced during cleavage of the $\alpha 1$, $\alpha 2$, $\beta 1$ and $\beta 2$ bond in the molecule of FIG. 1I according to an embodiment of the present invention.

DESCRIPTION OF PREFERRED EMBODIMENTS

The product spectrum obtained according to the invention can be characterized particularly readily by reference to the segments which are formally obtained by cleavage of the bond which is in the $\beta 1$ position relative to the double bond. In contrast to this, breakage of the bond in the $\alpha 2$ position (cf. FIG. 1) is substantially less significant with the result that the remaining hydrocarbon moiety (towards the chain end) is suitable as antimarker. Since a mixture is often present in the starting material, a mathematically complex method has to be carried out according to the invention in order to be able to determine the fraction of these segments.

Figure 1A:
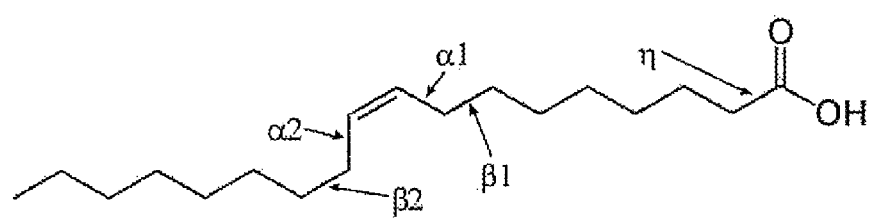
FIG. 1A shows oleic acid as starting material and the bonds in the $\alpha 1$, $\alpha 2$, $\beta 1$ and $\beta 2$ position relative to the double bond.
Figure 1B:
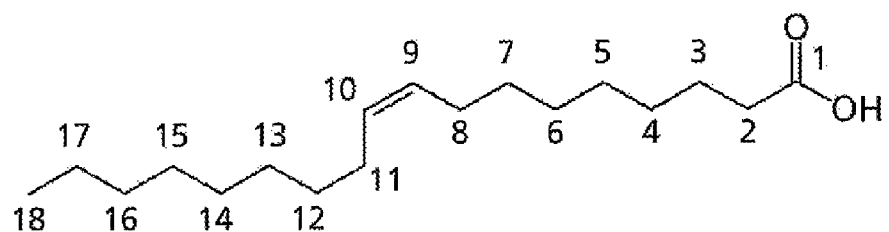
FIG. 1B shows the molecule of FIG. 1A with consecutive numbering of the carbon chain.
Figure 1C:
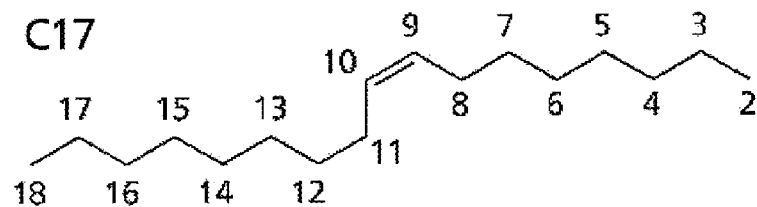
FIG. 1C shows a C17 fragment of the molecule of FIG. 1A following catalytic cracking according to the prior art.
Figure 1E:
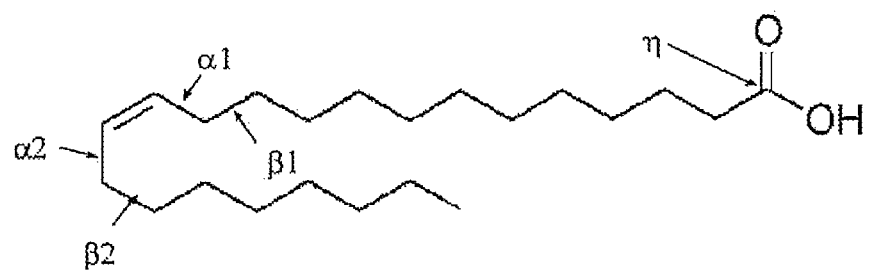
FIG. 1E shows erucic acid as starting material and the bonds in the $\alpha 1$, $\alpha 2$, $\beta 1$ and $\beta 2$ position relative to the double bond.
Figure 1F:
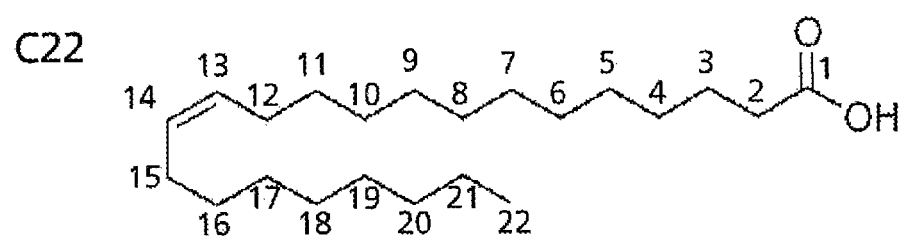
FIG. 1F shows the molecule of FIG. 1E with consecutive numbering of the carbon chain.
Figure 1G:
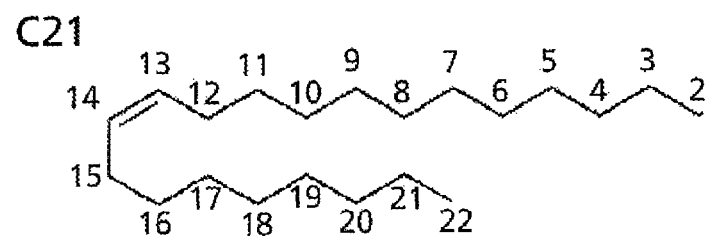
FIG. 1G shows a C21 fragment of the molecule of FIG. 1E following catalytic cracking.
Figure 1H:
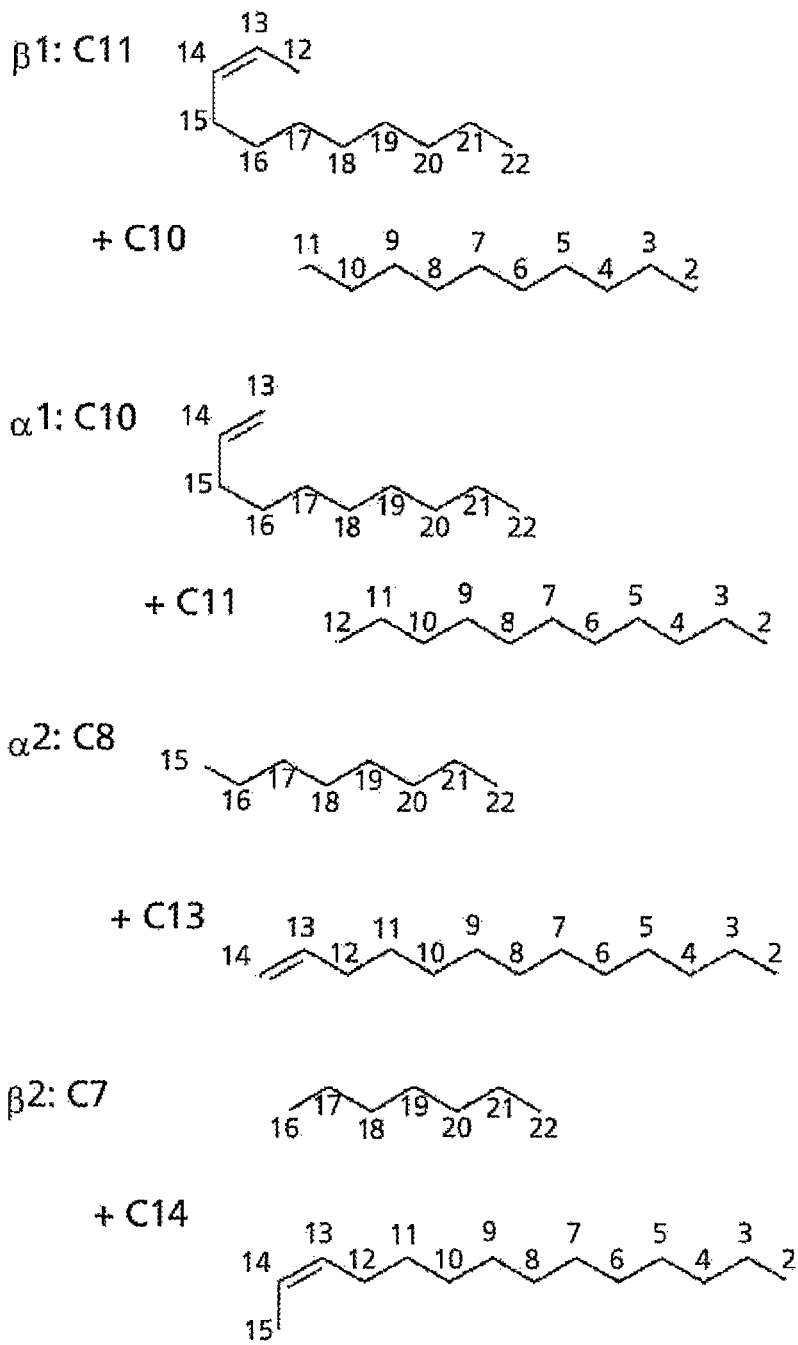
FIG. 1H shows products produced during cleavage of the $\alpha 1$, $\alpha 2$, $\beta 1$ and $\beta 2$ bond in the molecule of FIG. 1E according to an embodiment of the present invention.
Figure 1I:
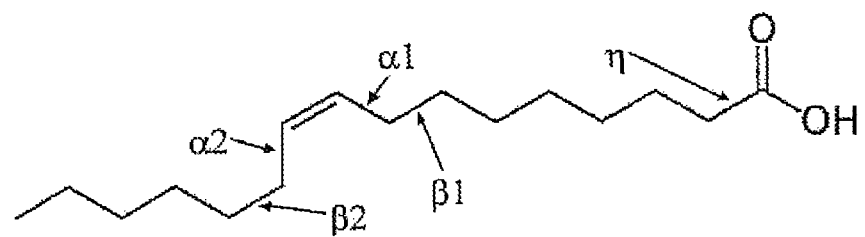
FIG. 1I shows palmitoleic acid as starting material and the bonds in the $\alpha 1$, $\alpha 2$, $\beta 1$ and $\beta 2$ position relative to the double bond.
Figure 1J:
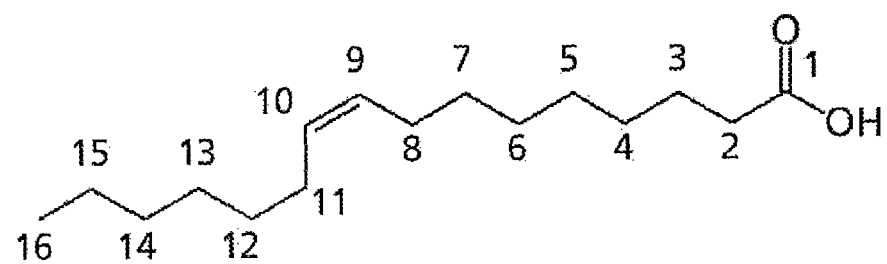
FIG. 1J shows the molecule of FIG. 1I with consecutive numbering of the carbon chain.
Figure 1K:
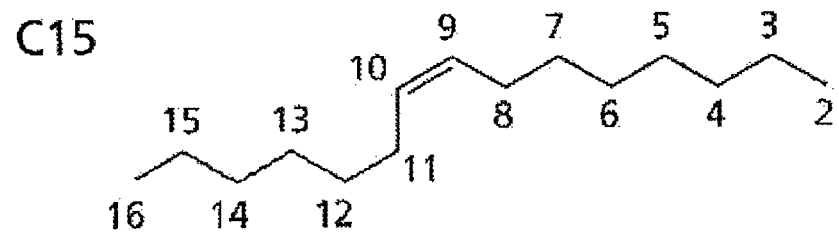
FIG. 1K shows a C15 fragment of the molecule of FIG. 1I following catalytic cracking.

For the purpose of explanation, reference is made to FIGS. 1A to 1L. FIG. 1A shows oleic acid as starting material and the bonds in the $\alpha 1$, $\alpha 2$, $\beta 1$ and $\beta 2$ position relative to the double bond. FIG. 1B shows the same molecule with consecutive numbering of the carbon chain. Upon catalytic cracking according to the prior art, only a breakage of the compound in $\eta$ position (cf. FIG. 1A) would be expected to an increased degree, thus giving a C17 fragment (cf. FIG. 1C). By contrast, in the method according to the invention, a different product spectrum is observed; here, besides a product with 11 carbon atoms, which is produced formally as a result of cleavage of the $\beta 1$ bond, increased formation of a product with 10 carbon atoms is also observed which arises formally as a result of cleavage of the $\alpha 1$ bond. FIG. 1D shows the products to be expected which are produced during cleavage of the $\alpha 1$, $\alpha 2$, $\beta 1$ and $\beta 2$ bond in FIG. 1A. Of the two expected products in each case, in particular the formation of the longer-chain product in each case is observed here, in FIG. 1D correspondingly the increased formation of C10 and C11 products. FIGS. 1E to 1H show the corresponding results for erucic acid as starting material (FIG. 1E) with the numbering according to FIG. 1F and the main product to be expected according to the prior art during catalytic cracking, of the C21 fraction (FIG. 1G), and the products to be expected for $\beta 1$, $\alpha 1$, $\alpha 2$ and $\beta 2$ cleavage (FIG. 1H). According to the invention, in particular C11 and C10 ($\beta 1$ cleavage and $\alpha 1$ cleavage) is formed. Finally, FIG. 1I to 1L shows the example of palmitoleic acid (FIG. 1I with numbering FIG. 1J), to be expected primary product from cracking according to the prior art (FIG. 1K) and the cleavage products which are produced by cleaving the $\alpha 1$, $\alpha 2$, $\beta 1$ and $\beta 2$ bond (FIG. 1L). In the case of increased $\beta 1$ and $\alpha 1$ cleavage, the fragments C8 and C9 are formed to an increased degree here.

According to the invention, the starting materials used are oxygen-containing hydrocarbons or hydrocarbon mixtures. Starting materials to be mentioned are in particular biogenic starting materials. Mention is to be made of for example lipids and fat-like compounds, with starting materials which comprise lipids and/or fat-like compounds being understood as meaning that the starting materials comprise, or consist of, lipids and/or essential constituents of lipids (such as mono- and diglycerides). According to the invention, the starting materials comprise at least 50% by weight of unsaturated oxygen-containing hydrocarbon compounds; this fraction can for example be determined by means of gas chromatography. These unsaturated oxygen-containing hydrocarbon compounds comprise the olefin fragments defined above. In order now to determine the fraction of the main component and the fraction of the optionally relevant other components $K_2$ to $K_x$, the fatty acid methyl ester determination ("FAME") known from biodiesel production, is carried out in accordance with the standard EN14214. For starting materials which, besides fatty acids and fatty acid esters, also comprise other unsaturated oxygen-containing hydrocarbon compounds, the contents of the olefin fragments according to the invention can also be determined.

The unsaturated oxygen-containing hydrocarbon compounds may be unbranched or branched compounds. Often, a high fraction of branched compounds is present since the fraction of the triglycerides will often also be high. Moreover, various olefin fragments present in the individual starting materials may either be completely unbranched, or else there may also be branched ones besides the unbranched ones (in specific cases it is also conceivable to only use branched olefin fragments). Such a branching of the olefin fragments can in particular consist in precisely one branching being present. For example a branching in the form of methyl groups may be present in the olefin fragment, in which case this branching is present either in the part fragment $C_xH_{2x}$ or $C_yH_{2y+1}$.

According to one embodiment, the olefin fragments of the unsaturated oxygen-containing hydrocarbon compounds that are used as starting material are selected such that the olefin fragments comprise essentially one constituent $C_yH_{2y+1}$, in which y is at least 5, in particular at least 6 and particularly preferably at least 7. Essentially here means that at least 90 mol % of the olefin fragments are present in this form. With starting materials in which y is at least 5, at least 6 or at least 7, the β1 cleavage forms hydrocarbon fragments in which the chain length is 8, 9 or 10 carbon atoms. Thus—at least with the β1 cleavage—hydrocarbons with medium chain lengths are formed.

In order to arrive at a high fraction of hydrocarbons with medium chain lengths, the fraction of unsaturated oxygen-containing hydrocarbon compounds in the starting material should be particularly high. Since it is assumed that starting materials which comprise a large fraction of fats and oils are often used, for example a fraction of >75% by weight of fats and oils, for example >90% by weight of fats and oils, determined by means of methyl ester determination (which is used as explained above in biodiesel production) can also serve to characterize starting materials which are particularly well suited for producing hydrocarbons with medium chain lengths. Therefore, according to one embodiment, the ratio of the monounsaturated fatty acids present in the starting material having at least 14 carbon atoms in the overall fatty acids present in the starting material is at least 30 mol %, in particular at least 50 mol %, for example at least 75 mol %.

According to the invention, a porous catalyst based on carbon is understood as meaning a substance whose surface has pores accessible for the starting material to be converted and the compounds present therein and which is able to cleave the starting material and the compounds present therein, and to catalytically assist the cleavage, respectively. Catalysts to be mentioned here are in particular fine pored carbon-containing materials (i.e. substances with pores having a diameter of less than or equal to 20 μm). Of these, preference is given according to the invention to substances which contain mesopores and/or micropores and/or submicropores (according to the IUPAC definition, mesopores have a pore diameter of 2-50 nm, micropores a pore diameter of 0.4-2 nm and submicropores a pore diameter <0.4 nm). Further suitable porous catalysts are in particular catalysts consisting essentially of carbon and other catalysts based on carbon. According to the invention, "based on carbon" is understood as meaning that (in relation to surface and reaction time) at least 90% of the surface which is catalytically active while carrying out step B) consists of carbon and/or of polycyclic aromatic hydrocarbons. Often, at least 99% of the catalytically active surface and often also the entire catalytically active surface will consist of carbon. This criterion is generally satisfied for catalysts consisting essentially of carbon and also for catalysts which consist essentially of inorganic substances if the duration of step B) (and thus the use time of the catalyst) is at least 30 minutes. "Essentially consisting of" is understood as meaning a catalyst which has at least 90% by weight, in particular at least 95% by weight, of inorganic substances and/or carbon.

According to the invention, contacting the starting material in the absence of oxygen can also be understood as meaning that besides the starting materials and optionally inert gas, generally no further gases are fed to the reactor. In particular, no hydrogenating agent, as is used for example during hydrocracking, is generally fed to the reactor. Independently of this, during part step B), however, as a result of the reaction of the starting material with the catalyst, it is possible that a product spectrum is formed in which compounds are present which themselves in turn have a reducing character (for example carbon monoxide).

According to an embodiment of the invention, the olefin fragments (according to formula I) having at least 14 carbon atoms present in the unsaturated oxygen-containing hydrocarbon compounds have a fraction >75 mol % of components K, for which it is the case that x is >4. The fraction of components K is determined here as explained above. Thus, according to this embodiment, the starting material contains an increased fraction of double bonds in hydrocarbon chains in which at least 6 carbon atoms are present between the heteroatom bonded to the $C_1$ atom and the double bond. An additional "antimarker" can then be defined in these compounds. These are the aliphatic product compounds $\epsilon_x$ which have y+6 carbon atoms. Here too, it is the case, as above, that initially the unbranched saturated product compounds are included as aliphatic product compounds $\epsilon_x$ and in addition all monounsaturated aliphatic product compounds with y+6 carbon atoms whose molar fraction is at least 10% of the amount of saturated product compound with y+6 carbon atoms. These product compounds $\epsilon_x$, however, can only serve as "antimarkers" for starting materials where x is >4 since in the event of a smaller x there is disturbance as a result of cleavage products of the exclusive cleavage in the η position (cf. FIGS. 1A, 1E and 1I), thus by the product which is formed by the pure decarboxylation for which still no cleavage of a bond has taken place in the vicinity of the double bond. The product compounds $\epsilon_x$ are determined here in accordance with the first alternative explained above for determining an increased fraction of hydrocarbons with medium chain lengths.

According to this first alternative, the second "antimarker" can then optionally also serve to characterize an increased fraction of the medium chain lengths. Also for the product compounds $\epsilon_x$ it is then possible to determine as above (according to the first alternative) the fraction $n_{\epsilon_x}$ of the main component and of the optionally present further components $K_2$ to $K_x$, and also to ascertain the averaged fraction $\overline{n_\epsilon}$. If the product compounds $\epsilon_x$ are used as antimarkers, then it applies additionally that $\overline{n_\beta} > \overline{n_\epsilon}$ (the average fraction of the marker components is thus greater than the average fraction of the second antimarker component). In the vast majority of cases, it additionally applies that $\overline{n_\beta} > 1.15 * \overline{n_\epsilon}$ (the fraction of the marker is thus at least 15% higher than that of the second antimarker) and in most cases it also applies that $\overline{n_\beta} > 1.25 * \overline{n_\epsilon}$ and often also that $\overline{n_\beta} > 1.5 * \overline{n_\epsilon}$ (the fraction of the marker is thus at least 25% or 50% greater than that of the antimarker).

According to a further embodiment, also a second marker can be used. According to the invention, it has been found that not only the product compounds with y+3 carbon atoms are formed to an increased degree, but in most cases also the product compounds with y+2 carbon atoms (even though often the average fraction of the product compounds with y+2 carbon atoms is less than that of the product compounds with y+3 carbon atoms). As described above for the marker in the first alternative for determining the increased fraction and hydrocarbons with medium chain lengths, it is also possible to determine for the second marker, the unbranched and saturated or monounsaturated aliphatic product compounds $\gamma_x$ with y+2 carbon atoms (which in turn are determined as defined above and/or are included or not included as regards the unsaturated product compounds), the fraction $n_{\gamma x}$ for the main component $K_1$ and optionally present further components $K_2$ to $K_x$ in each case and to use this to ascertain the averaged fraction $\overline{n_\gamma}$. If the second marker is also used, then it additionally applies that $\overline{n_\gamma} > \overline{n_\delta}$ and (if the fraction of components K with x>4 of the olefin fragments is >75 mol %) also $\overline{n_\gamma} > \overline{n_\epsilon}$. The fraction of the second marker is thus greater than that of the antimarker and of the second antimarker. In most cases, it additionally applies that $\overline{n_\gamma} > 1.15 * \overline{n_\delta}$, in particular $\overline{n_\gamma} > 1.25 * \overline{n_\delta}$, and independently of this—if the components optionally $\epsilon_x$ are included—also $\overline{n_\gamma} > 1.15 * \overline{n_\delta}$, in particular $\overline{n_\gamma} > 1.25 * \overline{n_\delta}$. (The fraction of the marker is thus in most cases 15% or 25% greater than that of the antimarker and, independently of this, but in most cases in addition to this, also the fraction of the second marker is 15% or 25% greater than that of the second antimarker). In most cases, it is moreover also the case that $\overline{n_\gamma} > 1.25 * \overline{n_\delta}$ and $\overline{n_\gamma} > 1.25 * \overline{n_\epsilon}$.

According to a further embodiment, moreover, the product compounds $\kappa_x$ and $\lambda_x$ (according to the above first alternative for determining the increased fraction of hydrocarbons with medium chain lengths) can also be included, in which case $\kappa_x$ stands for the product compounds with y+1 carbon atoms and $\lambda_x$ for the product compounds with precisely y carbon atoms. Here too, in turn only the unbranched saturated aliphatic product compounds and optionally according to the above procedure also the monounsaturated unbranched aliphatic product compounds are included. From this it is possible to determine the averaged fraction $\overline{n_\kappa}$ and $\overline{n_\lambda}$. For these product compounds too it then applies that $\overline{n_\kappa} > \overline{n_\delta}$ and additionally $\overline{n_\lambda} > \overline{n_\delta}$. In most cases, however, the fraction $\overline{n_\lambda}$ is less than $\overline{n_\beta}$ and often additionally also the fraction $\overline{n_\kappa} < \overline{n_\gamma}$. Often, independently of this, it additionally applies that $\overline{n_\kappa} < \overline{n_\beta}$ and often also that $\overline{n_\kappa} < \overline{n_\gamma}$. In other words, it is often observed that the fraction of product compounds β is greater than that of the product compounds γ and in addition also in most cases is greater than that of the product compounds κ and that of the product compounds λ. Depending on the starting material, the fraction of the product compounds κ, λ and/or γ can optionally however also be greater than those of the product compounds β. To characterize the product mixture and also the increased fraction of the medium chain lengths, however, it has proven useful to choose the product compounds β as markers since these have the greatest fraction in the majority of cases.

According to a further embodiment, the starting material provided in step A) is selected from the group consisting of fats, oils, fatty acids, fatty acid esters, tall oils, monoglycerides, diglycerides, alcohols and polyols, and also mixtures of the above materials with one another, and the mixture of said materials with other substances, although the aforementioned materials are present as the main component (i.e. with more than 50% by weight). The starting materials can also comprise terpenes, such as, for example, carotinoids or squalene. Suitable starting materials here are in particular bio-based starting materials, preferably bio-based fats and oils, which have the required fraction of olefin fragments.

According to the invention, fats and oils are to be understood as follows: solid, semisolid or liquid products of the plant or animal body which, moreover, are mostly more or less viscous, which consist in chemical terms essentially of mixtures of triglycerids of fatty acids with at least 14 carbon atoms, and small fractions of further substances. Essentially means here that at least 75% by weight, but often at least 90% by weight, for example at least 95% by weight, are present. Besides the triglycerides, for example acyl lipids (e.g. sterol esters) and unsaltable constituents may be present. In addition, foreign constituents (xenobiotics) such as mineral oils, softeners and/or biocides may also be present; on account of their lipophilic character, they accumulate in the fat. Fats are solid or semisolid substances at 20° C., oils are liquid at these temperatures. Together with the "fat-like compounds" (formerly lipoids), the fats and oils are summarized as belonging to the group of lipids.

According to the invention, a fatty acid is understood as meaning any aliphatic, saturated and unsaturated carboxylic acid, which may also be branched in particular cases.

According to an embodiment, the starting materials that are provided in step A) can consist at least in part or completely of waste substances, industrial coproducts and/or of renewable raw materials. Alternatively, these starting materials can also be produced from the aforementioned substances. In many cases, starting materials that are produced from renewable raw materials or are the renewable raw materials themselves will be used since substances which have the required fraction of olefin fragments can hereby be specifically cultivated or selected.

According to an embodiment, the starting material can therefore be selected from algae, cyanobacteria, bacteria and/or other plants with a high fraction of monounsaturated fatty acids. Alternatively, the starting materials can also be prepared from algae, cyanobacteria, bacteria and/or plants with a high fraction of monounsaturated fatty acids.

A particularly high fraction of olefin fragments which correspond to the above proviso can be achieved either by cultivating the plants or using specific plant varieties; alternatively, however, it is also possible for a targeted genetic modification of algae, cyanobacteria, bacteria or other plants to take place. Then, not only can the fraction, required according to the invention, of 50% by weight of unsaturated oxygen-containing hydrocarbon compounds be achieved, but even a fraction of at least 75% by weight, for example at least 90% by weight or in individual cases even at least 95% by weight.

According to an embodiment, the fraction of one, two or three acids selected from the group consisting of oleic acid, palmitoleic acid, erucic acid, based on all the fatty acids and fatty acid esters present in the starting material, is at least 50 mol %, in particular at least 75 mol %. Optionally, in the at least 50 mol %, in particular at least 75 mol %, alternatively or additionally one or more acids may also be present which form oleic acid, palmitoleic acid, erucic acid upon heating during step B) (for example ricinoleic acid).

The specified fatty acids are present in large amounts also in certain already obtainable starting materials. For example, high-oleic sunflower oil comprises a very high fraction of oleic acid, certain rape varieties comprise a very high fraction of erucic acid and additionally oleic acid (for example the rape used up to the start of the 1970s which could scarcely be used as food and feed on account of its high fraction of erucic acid) and cyanobacteria comprise a very high fraction of palmitoleic acid and/or corresponding fatty acid with 16 carbon atoms which has the cis double bond in position 7. Finally, mention is also to be made of high-oleic safflower oil with a fraction of monounsaturated fatty acids which is above 70%.

According to a further embodiment, the method according to the invention is carried out such that substances of value have already been removed beforehand from the starting material used in step A). In particular, the starting material is then preprocessed material prepared from waste substances, industrial coproducts and/or from renewable raw materials and is not used directly. The substances of value here that can be separated off are in particular polyunsaturated fatty acids and/or fatty concomitants. As already explained above, the desired product spectrum with an increased fraction of hydrocarbons with medium chain lengths can in most cases not be achieved from polyunsaturated fatty acids since these enter into undesired secondary reactions in step B). They can therefore be separated off from the starting material for food production for example. A separation can take place for example by means of the method described in EP 2 072 102 B1. This method is suitable in particular for separating off fatty concomitants, i.e. substances which can occur in a low concentration but have a high market value in pure form. Important representatives of fatty concomitants to be mentioned are in particular tocochromanols, carotinoids, sterols, lecithin and glucosinolates. Regarding further definitions of fatty concomitants and a possible method for separating them off, reference is made to EP 2 072 102 B1 in its entirety.

According to a further embodiment, carbon-based porous catalysts that can be used according to the invention are in particular catalysts which are selected from the group consisting of activated carbons, carbon molecular sieves, activated cokes, carbon nanotubes and mixtures of these substances with one another or mixtures of these substances with inorganic substances, in particular aluminum oxides, zeolites, perovskites, clays (e.g. phyllosilicates, e.g. saponites) and/or zinc chloride or else other porous or nonporous materials. The aluminum oxides, zeolites, perovskites and clays can be of natural and/or synthetic origin. A common aspect of all of the above catalysts is that they have a large surface area. Sometimes, the catalysts contain acidic centers, which may be advantageous for the cleaving of bonds.

Process step B) can be controlled particularly well if activated carbons are used. Here, both an adjustment of the pore sizes and pore distribution, as well as targeted doping or impregnation of the catalyst surface is possible in order to influence the cracking method in a targeted manner. The pore sizes can be enlarged for example by activation of the activated carbon. Thus, as a result of physical activation methods (e.g. steam activation), pores are available which are obtained by widening submicropores and very small micropores. As a result of chemical activation, even larger pores (in particular a larger fraction of mesopores) can also be obtained. As a result of the chemical and/or physical activation, some of the carbon is selectively degraded, as a result of which the desired pore structure arises. During gas activation (physical activation), optionally after a carbonization process, the catalyst starting material is activated at 800-1000° C. in a steam and/or carbon dioxide atmosphere. Here, some of the carbon is gassed and pores are generated which form a large internal surface area. In the case of chemical activation, e.g. phosphoric acid, zinc chloride or other dehydrating materials are used. Furthermore, it is also possible to use direct activates in which, in contrast to the shaped activated carbon, in which a carbon supplier is firstly combined in powder form with a binder, followed by a shaping and optionally a drying, a carbonization and an activation, activated granules are obtained directly from the carbon support by comminution and activation in an optionally interim carbonization step. This gives average pore sizes between those of chemically activated and physically activated active carbons.

Of particular suitability for the method according to the invention are in particular porous catalysts with a high fraction of micropores (radii of 0.2-0.4 nm), i.e. a micropore fraction which contributes with at least 800 $m^2$/g to the BET surface area.

According to an embodiment, the porous catalyst is doped and/or impregnated with a second catalyst. Doping is understood here as meaning that the second catalyst is added to the porous catalyst during its production, such that there is a homogeneous distribution of the second catalyst in the finished porous catalyst. By contrast, during the impregnation, a treatment takes place of the already finished porous catalyst with a material which comprises or consists of the second catalyst in such a way that the second catalyst is present only on the surface (also the pore surface) of the porous catalyst. As a result of doping and/or impregnation, chemically active substances can thus be introduced in a targeted manner into the pore system and/or the matrix of the catalyst which are able to change the chemical reactions over the catalyst. The doping or impregnation substances which can be introduced are in particular substances which themselves again have a catalytic effect; alternatively, it is also possible to introduce substances which alter the properties of the porous catalyst (for example the pH). Depending on the method used, the physical and adsorptive properties of the porous catalyst are likewise changed here. In order to remove harmful materials from the starting material, according to an embodiment of the method according to the invention, second catalysts can be added to the porous catalyst according to the invention which serve to remove these harmful substances or foreign substances and/or to convert them into gases that can be separated off. For example, catalysts which comprise manganese oxide can convert sulfur present in the starting material. As regards the production method of such catalysts doped with a second catalyst, and possible second catalysts, reference is made to WO 2007/137856 A2 (although this talks of doping substances instead of "second catalysts"). Reference is made to this document in its entirety.

According to an embodiment, the method according to the invention is carried out such that the starting substances are fed to the conversion reactor in liquid form. This has the advantage that an energy-intensive conversion of the unconverted starting material into the gas phase (or vapor phase) is not required. However, this variant usually requires pressures >2000 hPa.

According to an alternative embodiment, the starting material is converted in the vapor or gas phase into the conversion reactor. For example, for this purpose, a combined reaction and phase transfer apparatus is suitable in which an evaporation of the starting material and/or a decomposition of the starting material into vaporizable products and an evaporation of the decomposed starting material takes place; in the course of this application, this is called evaporator. In an evaporator of this kind, first cracking reactions can also already take place, particularly if molecules with large molecular weights are used. For example, mention can be made here of triglycerides; also in the case of undecomposed vaporizable compounds, however, initial cracking processes can already take place. Consequently, according to one embodiment, the method can be carried out such that the actual cracking reaction takes place only in the conversion reactor and in the evaporator as few as possible cracking processes take place. For this, the evaporation process can be carried out such that the starting material is pretreated (for example by saponifying triglycerides to give simple fatty acid esters) or by heating the starting material so slowly that evaporation does take place but decomposition does not. Furthermore, the average wall temperature of the evaporator can be chosen such that it corresponds to the current evaporation and/or decomposition temperature.

In a further embodiment, the method according to the invention can be carried out such that the contacting of the starting material with the porous catalyst takes place in the presence of water and/or a water-releasing material. By adding water or water-releasing materials, it is possible to increase the service life of the catalyst. The addition of water is therefore particularly useful for continuous processes. Preferably, at least enough water should be present that—based on the starting materials to be converted—at least one mole equivalent of water (in free form or in the form of water-releasing substances) is present. Quite generally, a water-releasing material is understood as meaning a substance or a substance mixture which either comprises bonded water which can be released or a substance or substance mixture which forms water by means of a chemical reaction, for example a condensation reaction (for example glycerol).

Water can be added in particular by introducing a stream of water or steam into the conversion reactor. Instead of water, it is also possible here to use water-containing substances or substances which eliminate water under the reaction conditions prevailing in the conversion reactor. The water, water-containing mixture or water-releasing material can also be added to the starting materials. Often, water is already present in the starting materials. Finally, the water or the water-releasing material can also be added to the inert gas stream.

Any desired, suitably heatable furnace can be used as conversion reactor. The conversion can take place continuously or discontinuously. Continuous operation is to be understood here as meaning that the introduction of starting materials takes place continuously. In particular, the starting materials can be added in gaseous form or vapor form. Suitable conversion reactors are thus fixed-bed reactors of any construction, moving beds, entrained-flow reactors, stationary and circulating fluidized-bed reactors (including jet mixers), rotary grate generators, shaft furnaces, multiple-hearth furnaces, rotary-tube reactors or tray reactors.

The porous catalyst can be arranged in the conversion reactor in any desired manner such that the substances to be converted can run through or over the catalyst. The contact of the liquid or vaporous starting materials with the porous catalyst can take place in any desired suitable manner, for example by spraying on liquid, cold or heating starting material, or by passing a gas stream with gaseous or vaporous starting substances through the bed. In some cases, a solid starting material will also be able to be placed directly onto the heated catalyst or directly into the conversion reactor. The catalyst can likewise be added continuously or discontinuously.

In order to render the reaction space inert, it should be flushed beforehand with a carrier gas. Suitable carrier gases are in particular an inert gas (such as nitrogen or carbon dioxide), water or water vapor or a $CO/CO_2$ mixture.

According to a further embodiment, the method is carried out at a pressure of at least 20 hPa. As a rule, in addition a pressure of 20 000 hPa is an expedient upper limit for the pressure. However, the method is often carried out at reduced pressures of at least 500 hPa or at elevated pressures of up to 3000 hPa (where reduced/increased refers to the atmospheric pressure of 1013 hPa). In particular, a selection of the pressure which is between 700 and 1300 hPa, for example between 800 and 1200 hPa, has proven to be suitable.

According to an embodiment, the feed mass stream (i.e. the stream of starting material converted into the vapor or gas phase) is adjusted at least according to one, in particular according to all three, of the following relations:

The feed mass stream per reaction chamber void volume (i.e. per volume of catalyst bed, which comprises catalyst solid, pore volumes and catalyst interstices) is 1.5 to 9 g/(l*min), in particular 2 to 8 g/(l*min), for example 4 to 6 g/(l*min).

The feed mass stream per catalyst mass is 2 to 30 mg/(g*min), in particular 6 to 18 mg/(g*min), for example 9 to 13.0 mg/(g*min).

The feed mass stream per catalyst mass [g] times catalyst surface [$m^2$/g] (BET surface area) is 1 to 20 g/(min*$m^2$), in particular 4-16 g/(min*$m^2$), for example 8-12 g/(min*$m^2$).

According to an embodiment, the reaction temperatures during step B) are in particular 250-600° C., for example 300-600° C., particularly preferably between 330 and 550° C., e.g. 350° C. and 500° C., often also 330-450° C. In addition, the temperature in the reactor is often selected such that it is at most 30° C., in particular at most 15° C., above the current prevailing evaporation temperature for the starting material at the selected operating pressure. As a result, a high liquid product yield is attained and a further chemical decomposition of the secondary cracking products is prevented.

In order to keep thermal decomposition as low as possible during reactions in the gas phase, it is possible to operate at atmospheric pressure or below atmospheric pressure. For this, the pressure is lowered at the temperatures between the evaporation temperature and 15 or 30° C. above the evaporation temperature, and only just a primary and secondary cracking is observed (where primary cracking is to be understood as meaning the decarboxylation). As regards a reactor temperature which is 15 or 30° C. above the evaporation temperature, evaporation temperature is thus defined according to the invention as that temperature at which at least 90% by weight of the fatty acids and glycerides present in the starting material evaporate or convert to the gas phase with decomposition. Preferably, the process is also carried out such that as little as possible or even no liquid starting material or liquid decomposition product formed from the starting material passes into the reactor.

According to a further embodiment, a hydrogenation and/or isomerization of the hydrocarbons present in the product mixture takes place before or after part step C). Also as a result of this, the product spectrum can be influenced in a targeted manner, meaning that a mixture of saturated and unsaturated or optionally also of branched or unbranched hydrocarbons is no longer present in the product spectrum, but only saturated hydrocarbons and/or a greater fraction of branched hydrocarbons.

Although a hydrogenation, which takes place simultaneously with step B), is possible according to the prior art, in the present case it would lead to rapid poisoning of the hydrogenation catalysts. Consequently, a hydrogenation—if desired—is carried out according to the invention after step B) and/or C). The hydrogenation takes place here in particular by means of a reaction with a hydrogen donor, in which a dehydrogenated form of the hydrogen donor is formed (e.g. naphthalene from decalin or naphthalene from tetrahydronaphthalene). The hydrogen donor can be added in gaseous form or liquid form, for example by injecting liquid decalin into the gaseous product mixture which has been obtained after step B) or C).

Further suitable hydrogen donors are hydroindoles (e.g. tetrahydroindole or dihydroindole), indane (which dehydrogenates to give indene), hydroquinolines or else aromatic systems with ethyl group, which is converted to a vinyl group as a result of the hydrogen elimination (e.g. ethylbenzene or ethylnaphthalene).

In individual cases, it is also possible to use a hydrogen donor which reacts primarily with short-chain unsaturated compounds (but not with long-chain unsaturated compounds), meaning that it can already be added to the starting material in step A) and then selectively reacts with the products of secondary cracking (i.e. the hydrocarbons of medium chain length), thus forming alkanes. In particular, hydrogen donors of this type are suitable for reacting terminal double bonds. Terminal double bonds of this kind can be formed especially in the case of $\alpha 1$ and $\alpha 2$ cleavages (cf. FIGS. 1A, 1E and 1I).

According to a further embodiment, the method according to the invention is carried out such that a regeneration of the catalyst takes place, especially after step B) has been carried out. The catalyst regeneration can take place in the reactor used for step B) or in an external reactor. During step B), depositions on the internal and external catalyst surfaces can arise. If these can be evaporated, a catalyst regeneration can be achieved merely by simply increasing the temperature to above the evaporation temperature, optionally supported by a pressure decrease and/or a carrier gas stream. In most cases, however, depositions cannot be evaporated at industrially relevant temperatures and are for example in the form of carbon. Carbon-containing catalysts are therefore post-treated so that they regain their catalyst properties as a result of a reactivation. Such a reactivation can, according to the prior art, be for example renewed activation with steam, carbon dioxide and, in special cases, also with oxygen. Here, an inert gas (e.g. nitrogen) can additionally be used as carrier gas and diluent gas. Depending on the properties of the carbon-containing catalyst and depending on the reactivation conditions, differences compared to the pore spectrum of the fresh catalyst may or may not be achieved in the regenerated catalyst. Incorrect reaction implementation may also lead to undesired fluctuations.

According to a further embodiment, the method is carried out in such a way that at least partly regenerated catalyst is used in step B). In order to ensure a continuous operation also as regards the catalyst, the reaction can be carried out such that step B) proceeds in two or more individually controllable reactors, of which at least one is operated in the "reaction" operating state and at least one is operated in the "regeneration" operating state. The mode of operation of the individual reactors is then switched round. For example in the case of a number of m reactors in the connection stage 1, the reactor 1 can be heated (or cooled) to the operating temperature, fresh, evaporated starting material can be fed to reactor 2, in reactor 3 the actual conversion reaction can take place and in reactor 4 a separation of the formed products and conveyance to a separating device can take place. In reactor 5 and any other reactors required for the regeneration, the 1 to n regeneration steps can then proceed. After the regeneration, optionally fresh catalyst can be added.

By virtue of such a procedure, the fresh starting material is passed over the freshly regenerated catalyst and if reaction step B) takes place in a plurality of reactors, the virtually depleted starting material/product mixture is passed over a catalyst which is just before the regeneration. Alternatively, however, the method can also be carried out such that the virtually depleted starting material/product mixture is passed over the freshly regenerated catalyst and the fresh starting material is passed over the catalyst which is just before the regeneration. It is of course also possible to draw off part streams from the individual reactors in the interim step or to add to these. Additionally, in a reactor the catalyst can also be discharged, meaning that an external regeneration takes place and regenerated or fresh catalyst can be introduced into a reactor. In an extreme case, adjacent reaction and/or regeneration steps can also coincide, meaning that the overall reaction is carried out in a first reactor and the overall regeneration is carried out in a second reactor.

The method according to the invention in accordance with one or more of the embodiments described above can be used particularly in order to use the resulting hydrocarbons of medium chain length as aviation fuel or to use them for producing aviation fuel. The hydrocarbons of medium chain length formed with the present method are exceptionally suitable not only on account of their boiling point for aviation fuels (which usually have a boiling point of 160-290° C.), in particular aviation fuels according the current standard Jet-A1, but also on account of the fact that, if these are not separated off in the separation device, there is always also a certain proportion of aromatics present in the product spectrum formed. Second-generation biokerosene produced according to the prior art initially comprises no aromatics since these are hydrogenated during the production process. For kerosene, these therefore have to be added again. To produce this second-generation biokerosene, vegetable oils are hydrogenated, whereas in the present method in the case of vegetable starting materials no hydrogenation takes place, but instead a cracking process, meaning that an altogether different product spectrum is obtained. Furthermore, the starting material according to the present method can be selected such that sulfur-containing substances are present. The kerosene customarily currently used comprises a certain fraction of sulfur which serves as lubricant (the sulfur fraction is often 3000 ppm). If then sulfur-containing starting material is selected for the method according to the invention, the sulfur can thus co-distill for example in the form of mustard oils and is therefore automatically present in the product spectrum.

Figure 3:
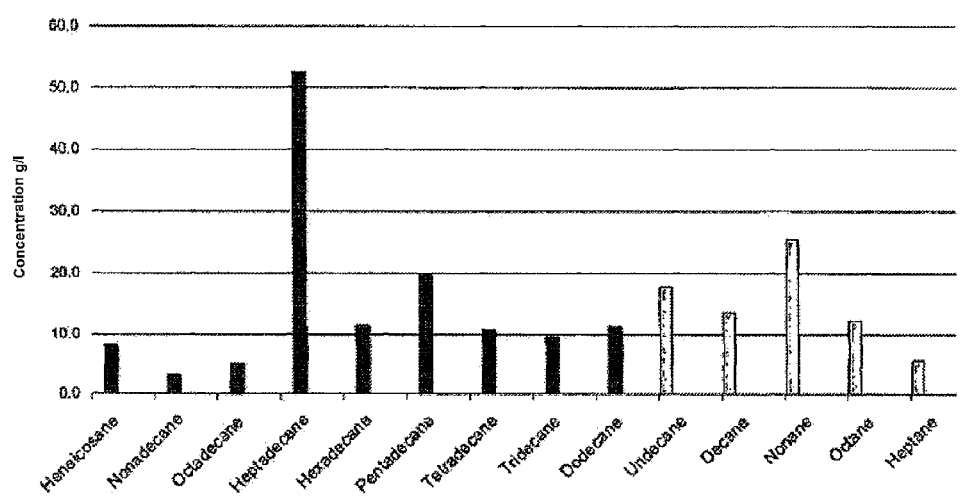
FIG. 3 shows concentrations of saturated and monounsaturated hydrocarbons produced according to an embodiment of the present invention where high-oleic safflower oil is the starting material.
Figure 4:
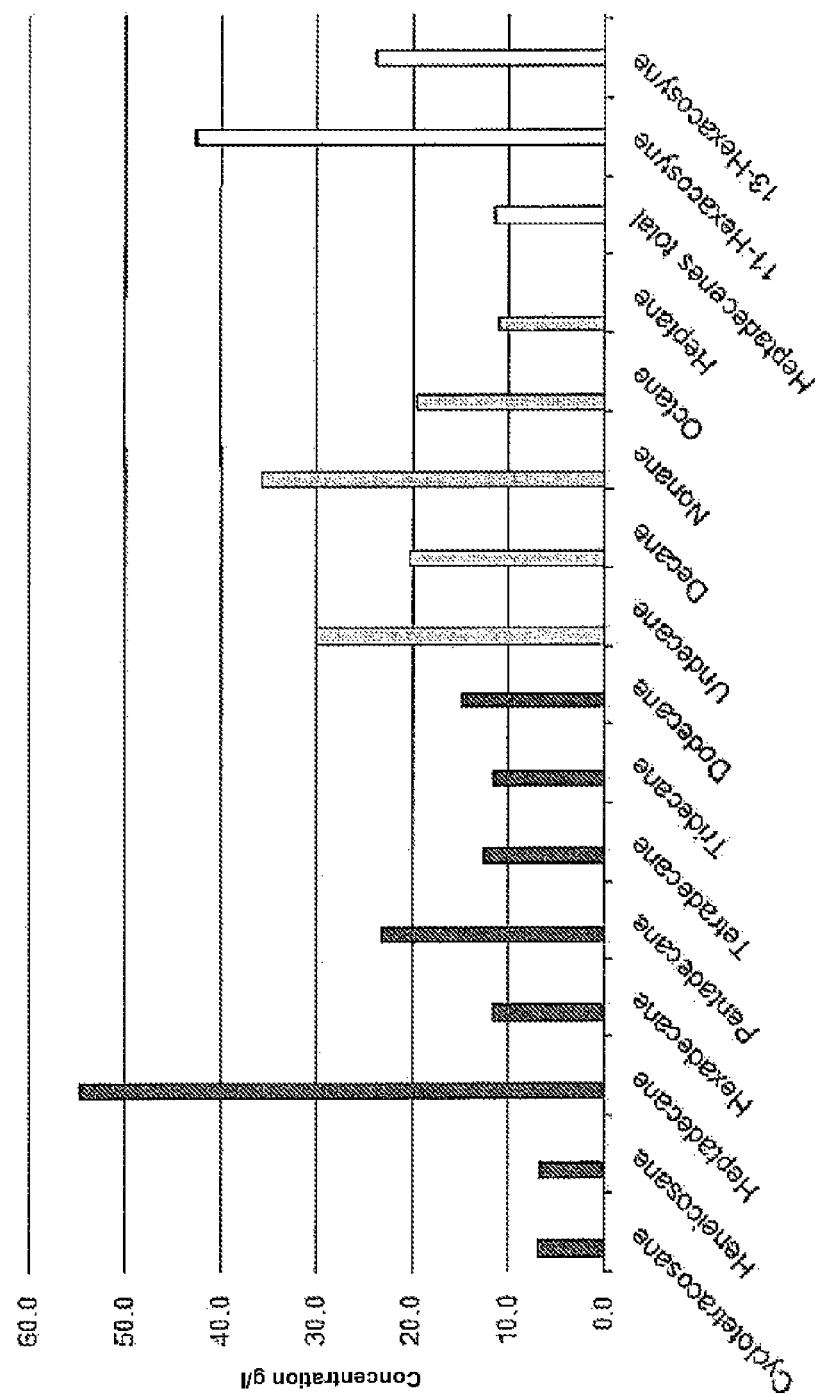
FIG. 4 shows concentrations of saturated and monounsaturated hydrocarbons produced according to an alternative embodiment of the present invention where high-oleic safflower oil is the starting material.

Further advantageous embodiments and developments of the invention arise below—without limiting the general nature—from the examples and FIGS. 2 to 4.

EXAMPLE 1—USE OF OLEIC ACID AS STARTING MATERIAL 316 g of oleic acid are introduced into an angled evaporation tube at a temperature of 425° C. spread evenly over 4 h with a preheating temperature of 70° C. The resulting vapors are passed over a fixed-bed catalyst in a downwardly directed stream. The fixed-bed catalyst used is 80 g of a steam-activated granular activated carbon based on coconut shells, with a specific surface area of 1100 $m^2/g$ (according to the BET method) and a density of about 450 g/l (here, the pores measured with BET occupy, according to the evaluation in accordance with Horvath and Kawazoe—J. Chem. Eng. Japan, 16, 6 (1983), 470-475—the following surface fraction: 0.2 to 0.3 nm (pore radius)—1101.3 $m^2/g$; 0.3 to 0.4 nm—223.7 $m^2/g$; 0.4 to 0.5 nm—87.3 $m^2/g$; 0.5 to 0.6 nm—46.5 $m^2/g$; 0.6 to 0.7 nm—24.1 $m^2/g$; 0.7 to 0.8 nm—12.1 $m^2/g$; 0.8 to 0.9 nm—6.7 $m^2/g$; 0.9 to 1.0 nm—4.1 $m^2/g$; 1.0 to 1.1 nm—3.9 $m^2/g$; greater than 1.1 nm and less than 0.2 nm—not measured). The granular activated carbon was charged to a steel reactor with a temperature of 450° C. Furthermore, 100 l/h of preheated nitrogen were introduced cocurrently to the reaction reactor with the oleic acid vapors (feed mass stream per reaction space empty volume: 5 g/(l*min)). The resulting product gases are fed to a cooling device and condensed. Table 1 gives the rough product fractions; the gas composition is shown in table 2; table 3 and FIG. 2 list the liquid products with the highest concentrations. Table 4 gives the concentrations of all saturated and monounsaturated C7-C11, C14 and C17 hydrocarbons. In all cases (as also in FIGS. 3 and 4), they are the unbranched compounds in each case.

TABLE 1

| Product | Fraction [% by weight] |
| --- | --- |
| organic liquid product | 58 |
| gaseous product | 28 |
| mass growth activated carbon | 8 |
| water | 6 |

TABLE 2

| Substance | Fraction in the product gas [mol %] |
| --- | --- |
| methane | 7.9 |
| ethane | 3.6 |
| ethylene | 1.7 |
| propane | 3.4 |
| propylene | 2.5 |
| n-butane | 3.0 |
| isopentane | 0.1 |
| n-pentane | 2.1 |
| heptane | 0.1 |
| carbon dioxide | 21.1 |
| carbon monoxide | 47.5 |
| hydrogen | 7.0 |

TABLE 3

| Substance | Concentration in the organic liquid product [g/l], determined by means of gas chromatography (GC) |
| --- | --- |
| heptadecane | 31.0 |
| hexadecane | 7.4 |
| pentadecane | 14.4 |
| tetradecane | 8.7 |
| tridecane | 8.5 |
| dodecane | 10.9 |
| undecane | 20.7 |
| decane | 17.2 |
| nonane | 18.7 |
| octane | 14.4 |
| heptane | 7.5 |
| (Z)-7-hexadecene | 2.4 |
| 2- and 5-dodecene | 4.6 |
| 3- and 5-undecene | 5.8 |
| 1-methylnaphthalene | 2.3 |
| naphthalene | 2.2 |
| dodecylbenzene | 3.6 |
| nonylbenzene | 3.5 |
| 1-ethyl-2-methylbenzene | 3.2 |

TABLE 4

| Substance | Concentration [% by mass] in the organic liquid product, determined by GC | | Concentration [% by mass] in the organic liquid product, determined by GC |
| --- | --- | --- | --- |
| heptadecane | 3.9 | C17 | 6.5 |
| heptadecenes | 2.6 | | |
| tetradecane | 1.1 | C14 | 1.8 |
| tetradecenes | 0.7 | | |
| undecane | 2.6 | C11 | 5.2 |
| undecenes | 2.6 | | |
| decane | 2.2 | C10 | 3.7 |
| decenes | 1.5 | | |
| nonane | 2.3 | C9 | 3.3 |
| nonenes | 1.0 | | |
| octane | 1.8 | C8 | 2.9 |
| octenes | 1.1 | | |
| heptane | 0.9 | C7 | 1.5 |
| heptenes | 0.6 | | |

All measurements were determined by averages of 12 measurements.

It is found that for pure oleic acid, besides the pure decarboxylation product heptadecane, undecane and undecene (i.e. the product compounds β with y+3=11 carbon atoms) are formed to an increased extent. Furthermore, a relatively large amount of decane and decene is formed (i.e. product compound γ with y+2=10 carbon atoms). In addition, an increased fraction of nonane, nonene and also octene and octane is also to be noted (product compounds κ and λ). By contrast, the heptane fraction is relatively low (product compounds δ with y−1=7 carbon atoms). Furthermore, there is also a relatively small fraction of tetradecane and tetradecene (i.e. the product compounds ε).

Figure 2:
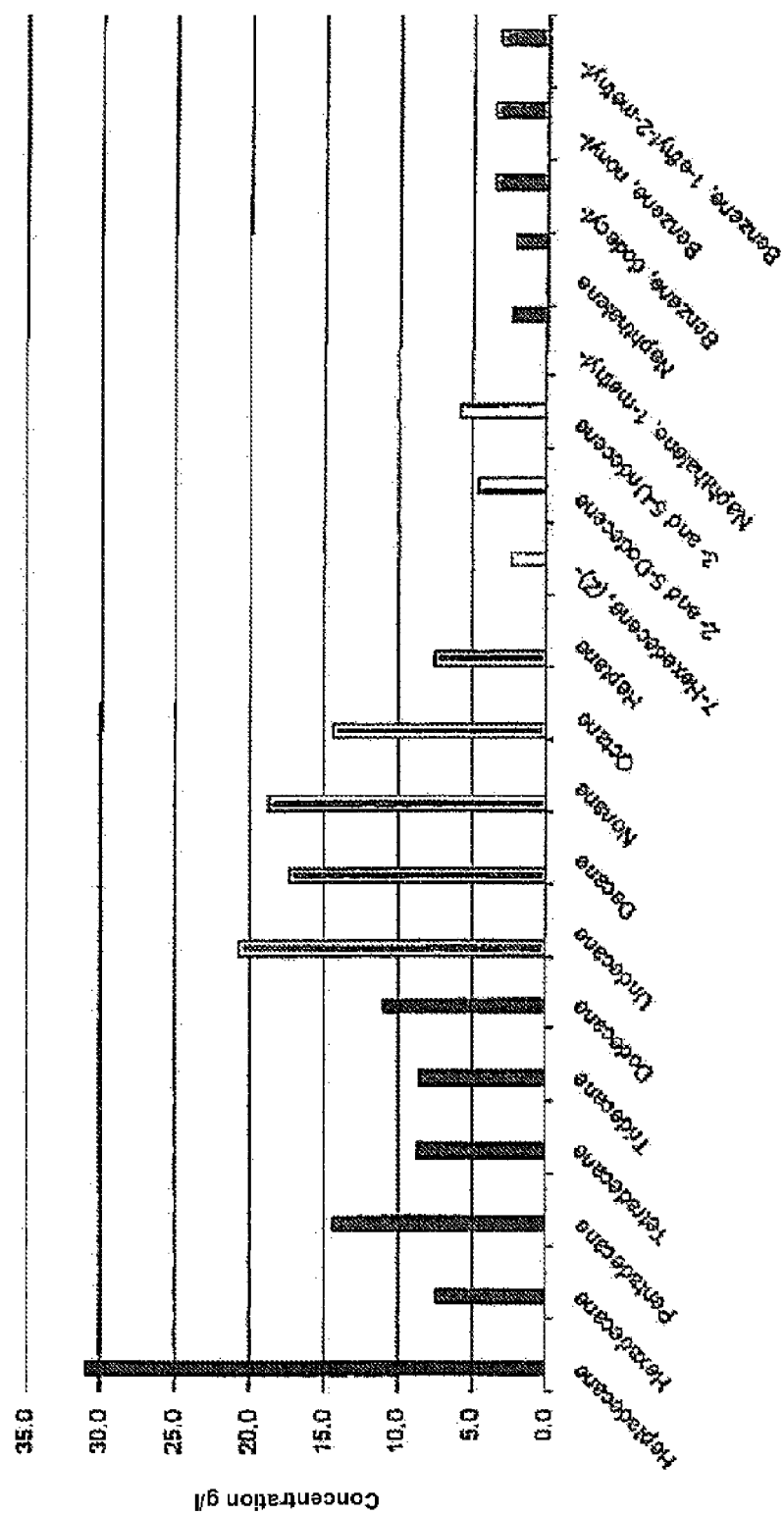
FIG. 2 shows the concentration percentage of liquid products of an embodiment of the present invention where oleic acid is the starting material.

Example 1 shows that for a pure starting compound, i.e. a compound in which only one main component $K_1$ is present to 100% as olefin fragment, product components with 11—and likewise also with 10 and 9—carbon atoms are formed to an increased extent, where as a result of the considerable formation of undecenes, the $C_{11}$ component arises to a particularly high extent—in FIG. 2 the bars for undecane and the undecene are to be calculated together for this purpose and achieve virtually the value for the pure decarboxylation product by cleavage of the bond η, namely heptadecane.

EXAMPLE 2—USE OF HIGH-OLEIC SUNFLOWER OIL AS STARTING MATERIAL

Example 2 was carried out as Example 1 except that instead of pure oleic acid high-oleic sunflower oil was used. The oleic acid here constitutes a fraction of more than 80 mol % of the present fatty acids; here too, only the olefin fragment corresponding to the oleic acid is present as main fragment $K_1$. Further olefin fragments with a fraction of at least 5 mol % of the mixture of olefin fragments are not present here. The liquid product yield is 62% by weight.

As already shown in Example 1, it is also evident here (cf. FIG. 3) that the fraction of undecane and decane is increased considerably compared with the fraction of heptane and tetradecane. On account of the selected starting material, a significantly increased peak for nonane is also evident here. Table 5 lists the concentrations of the saturated and monounsaturated C7-C11, C14 and C17 hydrocarbons ascertained by GC.

TABLE 5

| Substance | Conc. [% by mass] in the organic liquid product | | Conc. [% by mass] in the organic liquid product |
|---|---|---|---|
| heptadecane | 6.6 | C17 | 9.8 |
| heptadecenes | 3.2 | | |
| tetradecane | 1.3 | C14 | 1.8 |
| tetradecenes | 0.2 | | |
| undecane | 2.2 | C11 | 3.3 |
| undecenes | 1.1 | | |
| decane | 1.7 | C10 | 2.2 |
| decenes | 0.5 | | |
| nonane | 3.2 | C9 | 3.8 |
| nonenes | 0.6 | | |
| octane | 1.5 | C8 | 2.0 |
| octenes | 0.5 | | |
| heptane | 0.7 | C7 | 1.0 |
| heptenes | 0.3 | | |

All measurements were determined by averages of 12 measurements.

EXAMPLE 3—USE OF HIGH-OLEIC SAFFLOWER OIL AS STARTING MATERIAL

Example 3 was carried out like Example 1 except that instead of pure oleic acid high-oleic safflower oil and a different catalyst were used. The high-oleic safflower oil has a fraction of oleic acid of at least 70% by weight; the fraction of monounsaturated fatty acids is 75% by weight. Here too, only the olefin fragment corresponding to the oleic acid is present as main fragment $K_1$. Further olefin fragments with a fraction of at least 5 mol % in the mixture of the olefin fragments are not present here.

The fixed-bed catalyst used is 80 g of a steam-activated shaped activated carbon based on wood carbon which has a specific surface area of 1250 m²/g (according to the BET method), a tap density of 430 g/l (determined in accordance with DIN EN ISO 787-11) and the specific cumulative surface area of the micropores according to Horvath and Kawazoe of 1420 m²/g. The liquid product yield is 58% by weight.

As already shown in Examples 1 and 2, it is again evident here (cf. FIG. 4) that the fraction of undecane and decane is increased considerably compared to the fraction of heptane and tetradecane. On account of the selected starting material, a significantly increased peak for nonane is also evident here. Table 6 lists the concentrations of the saturated hydrocarbons with 7 to 11 and also with 14 carbons atoms ascertained by GC. The concentrations of the corresponding monounsaturated hydrocarbons was not determined, but they are in any case below 0.8% by mass in each case.

TABLE 6

| Substance | Conc. [% by mass] in the organic liquid product | Substance | Conc. [% by mass] in the organic liquid product |
|---|---|---|---|
| heptadecane | 6.8 | decane | 2.5 |
| heptadecenes | 1.4 | nonane | 4.5 |
| tetradecane | 1.6 | octane | 2.4 |
| undecane | 3.8 | heptane | 1.4 |

Figure 5:
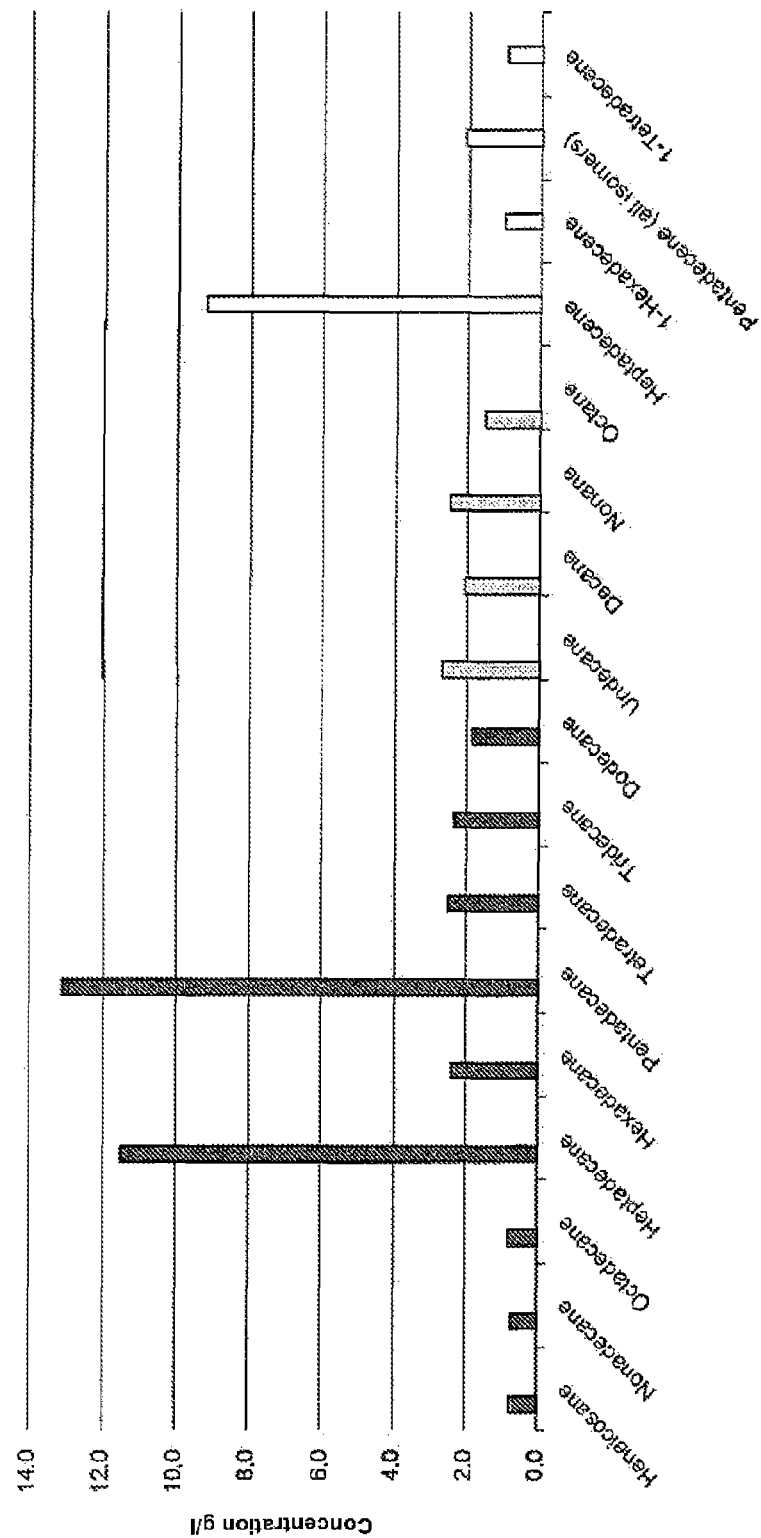
FIG. 5 shows concentrations of saturated and monounsaturated hydrocarbons produced according to the prior art.

EXAMPLE 4—COMPARATIVE EXAMPLE 300 g of mixed old fat were introduced into an angled evaporation tube spread evenly over 6 h. The old fat comprised high fractions of stearic acid and palmitic acid and insignificant fractions of oleic acid. 65 g of the catalyst from Example 1 were used. All of the other experimental conditions were as in Example 1. The yield of organic liquid phase here was 55% by weight. FIG. 5 shows the resulting product spectrum.

It is found that there is no increased formation of undecane and decane here. The fraction of tetradecane (i.e. of the "antimarker") is approximately the same as that of undecane.

The invention claimed is:

1. A method for producing pure hydrocarbons selected from the group of compounds having 8 to 16 carbon atoms or of hydrocarbon mixtures with an increased fraction of hydrocarbons having medium chain lengths which are selected from the group of compounds having 8 to 16 carbon atoms, comprising the steps of:

A) providing a starting material comprising at least 50% by weight of unsaturated oxygen-containing hydrocarbon compounds, where the unsaturated oxygen-containing hydrocarbon compounds contains at least partially monounsaturated olefin fragments which are selected from fragments having at least 14 carbon atoms and correspond to the formula —$C_1$-$C_xH_{2x}$—CH=CH—$C_yH_{2y+1}$, wherein x and y are integers, where x is greater than 1 and y is greater than 0, carbon atom $C_1$ is saturated with at least one of substituted or unsubstituted heteroatoms and hydrogen, and wherein the olefin fragment comprises a main component $K_1$ with a fraction of $k_1$ mol % and optionally further components $K_2$-$K_x$ with a fraction of $k_2$-$k_x$ mol %, which is at least 5 mol %, and providing a carbon-based porous catalyst with a fraction of micropores which contributes with at least 800 m²/g to the BET surface area;

B) contacting the starting material, in the absence of oxygen, with the porous carbon-based catalyst in a conversion reactor at a pressure from 20 to 20,000 hPa and at a temperature of 200-800° C., wherein the resulting hydrocarbon-containing product mixture comprises an increased fraction of product compounds of hydrocarbons with medium chain lengths, where the increased fraction is detected by a) determining for the main component $K_1$ and each further component $K_2$-$K_x$
   the unbranched and saturated or monounsaturated aliphatic product compounds $\beta_x$ with y+3 carbon atoms, and
   the unbranched and saturated or monounsaturated aliphatic product compounds $\delta_x$ with y−1 carbon atoms,
b) determining the fractions $n_{\beta_x}$ and $n_{\delta_x}$ for the product compounds $\beta_x$ and $\delta_x$ in the product mixture, and
c) calculating the averaged fraction $\overline{n_\beta}$ for the product compounds $\beta_x$ and the average fraction $\overline{n_\delta}$ for the product compounds $\delta_x$ according to the formula $$\overline{n} = \sum_{i=1}^{x} k_i * n_i,$$

d) wherein an increased fraction of product compounds being hydrocarbons with medium chain lengths is present if it applies that $\overline{n_\beta} > 1.15 * \overline{n_\delta}$ and preferably that $\overline{n_\beta} > 1.5 * \overline{n_\delta}$; and C) collecting the hydrocarbon-containing product mixture and conveying the hydrocarbon-containing product mixture to a separating apparatus in which a product separation takes place.

2. The method according to claim 1, wherein the olefin fragments contain a fraction greater than 75 mol % of components K with x being greater than 4, and further comprising the step of determining the unbranched and saturated or monounsaturated aliphatic product compounds $\epsilon_x$ with y+6 carbon atoms, the fraction $n_{\epsilon_x}$, and the averaged fraction $\overline{n_\epsilon}$ for the main component $K_1$ and each further component $K_2$-$K_x$ with x being greater than 4, and, and wherein $\overline{n_\beta} > \overline{n_\epsilon}$.

3. The method according to claim 1, further comprising the step of determining unbranched and saturated or monounsaturated aliphatic product compounds $\gamma_x$ with y+2 carbon atoms, fraction $n_{\gamma_x}$, and averaged fraction $\overline{n_\gamma}$ for the main component $K_1$ and each further component $K_2$-$K_x$, and wherein $\overline{n_\gamma} > \overline{n_\delta}$ and optionally $\overline{n_\gamma} > \overline{n_\epsilon}$.

4. The method according to claim 1, wherein the starting material is selected from the group consisting of fats, oils, fatty acids, fatty acid esters, tall oils, monoglycerides, diglycerides, alcohols and polyols and mixtures thereof.

5. The method according to claim 1, wherein the starting material is obtained from waste materials, industrial coproducts, or renewable raw materials.

6. The method according to claim 5, wherein the starting material is obtained from at least one of algae, cyanobacteria, bacteria and plants with a high fraction of monounsaturated fatty acids.

7. The method according to claim 6, wherein the at least one of algae, cyanobacteria, bacteria and plants are genetically modified.

8. The method according to claim 7, wherein the fraction of monounsaturated fatty acids having at least 14 carbon atoms is at least 40 mol % based on fatty acids present in the starting material.

9. The method according to claim 7, wherein a fraction of oleic acid, palmitoleic acid, erucic acid, or any mixtures thereof is at least 50 mol % based on the fatty acids present in the starting material.

10. The method according to claim 7, wherein at least one of polyunsaturated fatty acids and fatty concomitants—are separated from the starting material prior to performing step A).

11. The method according to claim 1, wherein the porous catalyst is selected from the group consisting of activated carbons, carbon molecular sieves, activated cokes, carbon nanotubes, mixtures thereof or mixtures of these substances with aluminum oxides, zeolites, perovskites and zinc chloride.

12. The method according to claim 1, wherein the starting material is fed to an evaporation device prior to being contacted with the porous catalyst.

13. The method according to claim 1, wherein a hydrogenation or isomerization of the hydrocarbons present in the product mixture is carried out before product separation.

14. The method according to claim 1, wherein at least one of hydrogenation and isomerization of the hydrocarbons present in the product mixture is carried out after product separation.

15. The method according to claim 1, wherein a regeneration of the porous catalyst is carried out following step B).

16. The method according to claim 1, wherein the porous catalyst is an at least partially regenerated catalyst.

17. The method according to claim 2, wherein $\overline{n_\beta} > 1.25 * \overline{n_\epsilon}$.

* * * * *